(12) United States Patent
Bonnet et al.

(10) Patent No.: US 10,744,327 B2
(45) Date of Patent: Aug. 18, 2020

(54) ACTIVE ELECTRICAL NERVE STIMULATION MEDICAL DEVICE, WITH AUTOMATIC CHARGE COMPENSATION CONTROL

(71) Applicant: SORIN CRM SAS, Clamart (FR)

(72) Inventors: Jean-Luc Bonnet, Massy (FR); Laure Duchemin Laporte, Morangis (FR); Arnaud Follenius, Paris (FR)

(73) Assignee: Sorin CRM SAS, Clamart (FR)

( * ) Notice: Subject to any disclaimer, the term of this patent is extended or adjusted under 35 U.S.C. 154(b) by 154 days.

(21) Appl. No.: 16/060,904

(22) PCT Filed: Dec. 6, 2016

(86) PCT No.: PCT/EP2016/079837
§ 371 (c)(1),
(2) Date: Jun. 8, 2018

(87) PCT Pub. No.: WO2017/097739
PCT Pub. Date: Jun. 15, 2017

(65) Prior Publication Data
US 2018/0353760 A1    Dec. 13, 2018

(30) Foreign Application Priority Data

Dec. 11, 2015  (FR) .................................. 15 62184

(51) Int. Cl.
*A61N 1/36*    (2006.01)
*A61N 1/02*    (2006.01)
(Continued)

(52) U.S. Cl.
CPC ......... *A61N 1/36139* (2013.01); *A61N 1/025* (2013.01); *A61N 1/08* (2013.01);
(Continued)

(58) Field of Classification Search
CPC .............. A61N 1/3716; A61N 1/36139; A61N 1/36146–36157; A61N 1/36164; A61N 1/36178
See application file for complete search history.

(56) References Cited

U.S. PATENT DOCUMENTS 4,373,531 A * 2/1983 Wittkampf ............. A61N 1/371
                                                                607/13
4,821,724 A * 4/1989 Whigham .............. A61N 1/365
                                                                607/13
(Continued)

FOREIGN PATENT DOCUMENTS

EP    2 926 863 A1    10/2015

OTHER PUBLICATIONS

International Search Report and Written Opinion on International Patent Application No. PCT/EP2016/079837 dated Jun. 15, 2017. 8 pages.

*Primary Examiner* — Kennedy Schaetzle
(74) *Attorney, Agent, or Firm* — Foley & Lardner LLP

(57) ABSTRACT

This disclosure relates to an active medical device which includes a generator for producing multiphase nerve stimulation pulse trains, each pulse train including at least one stimulation pulse preceded by a precharge pulse and ending with a passive discharge pulse. The active medical device also includes a sensor configured to output a control signal representative of a physiological and/or physical parameter capable of being influenced by the output of nerve stimulation pulse trains. The active medical device also includes an automatic charge compensation control circuit configured to receive at the input the control signal output by the sensor, determine an amplitude and/or a precharge pulse time as a function of at least one predetermined criterion, and output to the generator a precharge pulse control signal to be produced at the output.

11 Claims, 14 Drawing Sheets

(51) Int. Cl.
*A61N 1/08* (2006.01)
*A61N 1/39* (2006.01)
*A61B 5/0428* (2006.01)
*A61N 1/372* (2006.01)

(52) U.S. Cl.
CPC ...... *A61N 1/36053* (2013.01); *A61N 1/36114* (2013.01); *A61N 1/36125* (2013.01); *A61N 1/36128* (2013.01); *A61B 5/04288* (2013.01); *A61N 1/36157* (2013.01); *A61N 1/37235* (2013.01); *A61N 1/37252* (2013.01); *A61N 1/3962* (2013.01); *A61N 2001/083* (2013.01)

(56) References Cited

U.S. PATENT DOCUMENTS

| | | |
|---|---|---|
| 2009/0048643 A1 | 2/2009 | Erickson et al. |
| 2010/0114198 A1 | 5/2010 | Donofrio et al. |

* cited by examiner

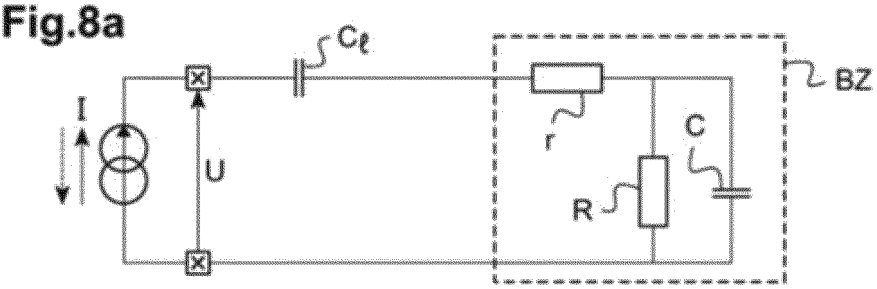
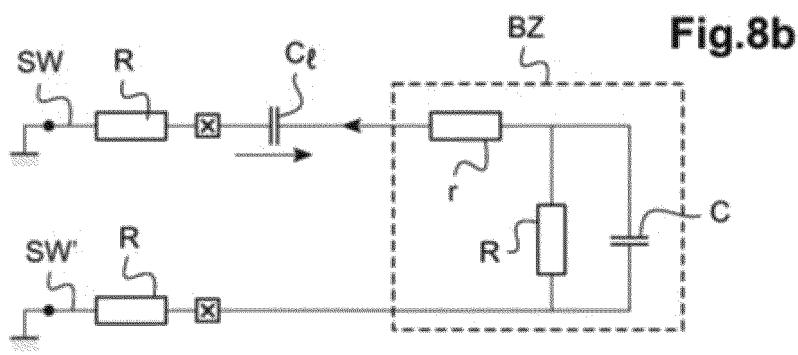
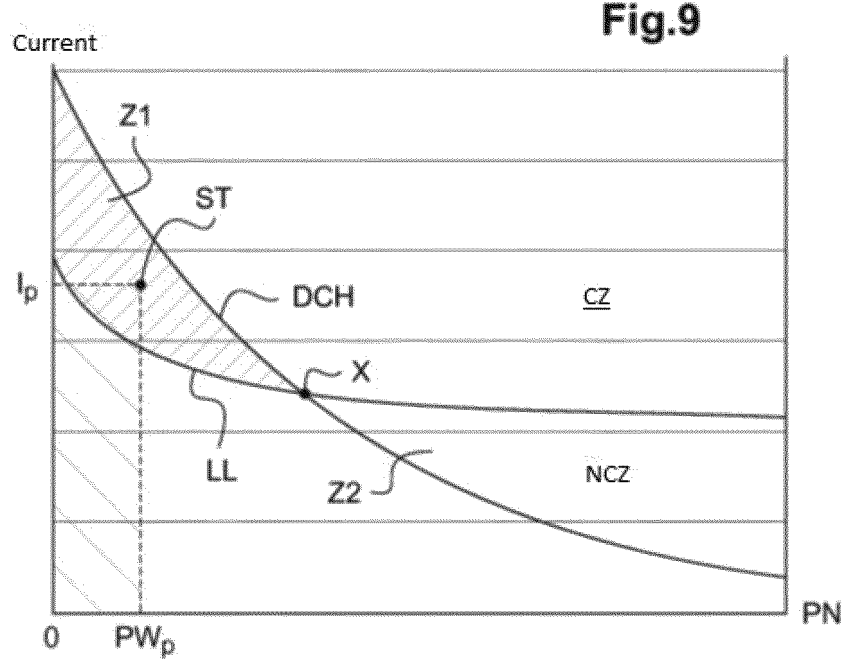

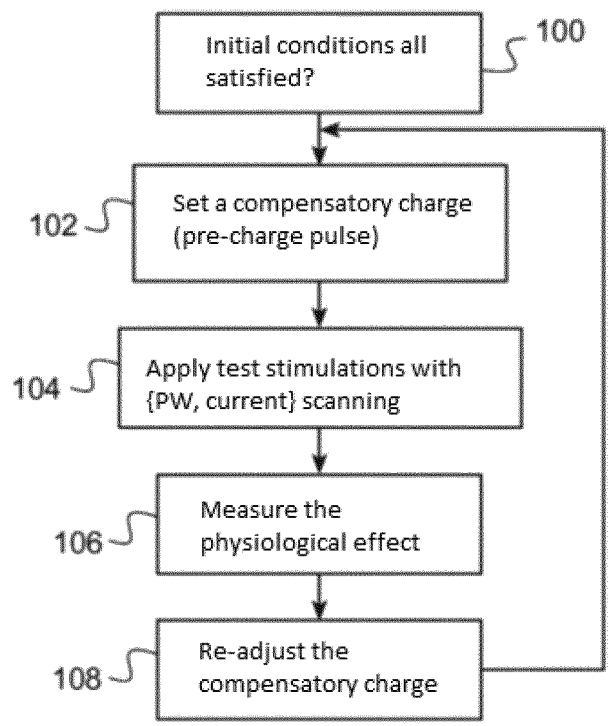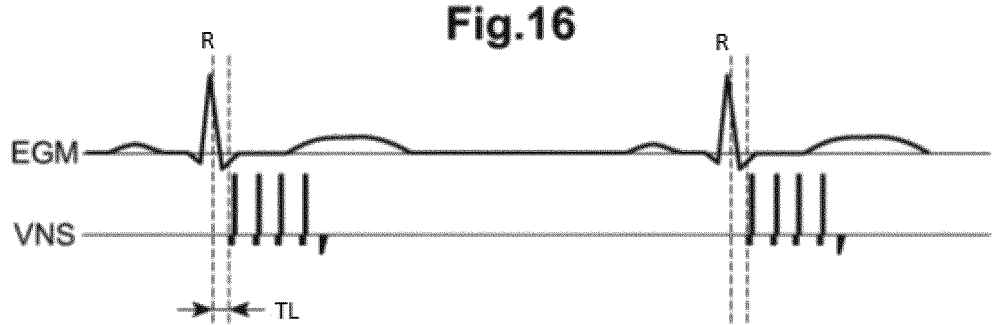

ACTIVE ELECTRICAL NERVE STIMULATION MEDICAL DEVICE, WITH AUTOMATIC CHARGE COMPENSATION CONTROL

CROSS-REFERENCE TO RELATED APPLICATIONS

This application is a 371 U.S. National Application of International Application No. PCT/EP2016/079837, filed Dec. 6, 2016, which claims the benefit of and priority to French Patent Application No. 1562184, filed Dec. 11, 2015, which is incorporated herein by reference in its entirety.

BACKGROUND

The invention relates to "active medical devices" as defined by Council of the European Communities Directive 90/385/EEC of 20 Jun. 1990.

It relates more specifically to implants making it possible to deliver, i.e. to administer, Functional Electrical Stimulation (FES) therapies, consisting in applying stimulation in the form of repeated electric pulses to organs for therapeutic purposes.

The invention relates more particularly to implants making it possible to deliver therapies for stimulating biological tissues. The invention relates more specifically to stimulating the nervous system (such stimulation being generally referred to below as "neurostimulation"), particularly but non-limitingly Vagus Nerve Stimulation (VNS), by means of a device comprising a lead provided with an electrode implanted on the vagus nerve or in the vicinity thereof, and a generator that delivers VNS electric pulses to said electrode.

EP 2 926 863 A1 (Sorin CRM) describes such a VNS generator for stimulating the vagus nerve.

However, such use is not limiting, and the invention is applicable to other situations in which biological tissue stimulation requires compensation pulses to be delivered.

Stimulating the nervous system is a therapeutic approach that is recognized or that is being evaluated for a large number of disorders such as epilepsy, major depression, pain, heart failure, sleep apnea, obesity, etc. VNS has demonstrated positive effects in preclinical trials for heart failure, where it acts on the autonomic nervous system, and, in secondary manner, on the cardiovascular functions, inducing a reduction in the heart rate and an increase in the ejection fraction of the left ventricle, thereby, in particular, making it possible to contribute to reducing the progress of cardiac remodeling that can give rise to a state of worsened heart failure.

Through its action on the sympathovagal balance (SVB) of the patient, neurostimulation also has a general effect on the vascular system, with vasoconstriction being modulated by modifying the diameters of the arteries and the peripheral resistance, resulting in a general vasodilation of the vascular system.

The neurostimulation pulses may optionally be delivered synchronously with the heart rate or with any other physiological parameter, in which case the device comprises means for collecting at least one physiological parameter, typically myocardial depolarization waves, which can be measured by collecting an electrocardiogram (ECG) using a subcutaneous electrode, an electrogram (EGM) using an electrode implanted on or in the myocardium, or a far-field signal collected between the housing and an electrode placed outside the heart, in particular a pole of the neurostimulation electrode placed on or in the vicinity of a nervous structure.

Since neurostimulation pulses are current pulses, when physiological tissue is stimulated, the interface between the electrode and the tissue should remain generally balanced in terms of electric charge.

With constant-current pulses, charge Q is defined as the product of the current I (in amps (A) or milliamps (mA)) multiplied by the duration or width PW of the pulse (in seconds (s) or milliseconds (ms)): $Q = I \times PW$, and is therefore expressed in coulombs, or more generally in microcoulombs ($\mu C$) in neurostimulation.

Since, due to the current flowing, delivery of the neurostimulation pulse proper (referred to below as the "stimulation phase") produces a creation and an accumulation of charge at the stimulation site, that charge needs to be compensated for or cancelled out by an opposite charge (by causing a current to flow in the direction opposite to the direction of the stimulation phase), in such a manner as to maintain the overall electrical neutrality of the stimulated tissue.

US2010/0114198 A1 describes a stimulation pulse generator incorporating a circuit that automatically performs such charge compensation.

The opposite compensation charge (referred to below as the "compensatory phase") may take place:
  passively, by a spontaneous discharge in the bioimpedance formed by the tissues at the stimulation site, this discharge (referred to below as "passive discharge") taking place after applying an isolated stimulation pulse or a burst of successive stimulation pulses; and/or
  actively, by a charge resulting from a current pulse generated by the stimulator and applied to the tissue before (pre-charge) or after ("post-charge") one or more stimulation pulses.

Such a combination of time phases comprising i) a stimulation phase and ii) a compensatory phase comprising at least one active pre-charge/post-charge or a final passive discharge is referred to as a "multi-phase pulse train".

The term "pre-charge pulse" is used below to designate a type of controlled compensatory pulse, but that term does not presuppose any particular type of multi-phase sequence of pulses, it being possible for the controlled compensatory phase to be generated not only before but also after a stimulation phase, regardless of whether said stimulation phase is formed of an isolated stimulation pulse or of a burst of stimulation pulses succeeding one another at a high rate.

In addition, various multi-phase profiles combining pre-charge and stimulation pulses may be considered, e.g. with a pre-charge pulse associated with each stimulation pulse, or a pre-charge pulse associated with a plurality of successive stimulation pulses, etc. it being specified that the invention is applicable to any type of stimulation profile combining a pre-charge (or post-charge) pulse, one or more stimulation pulse(s), and a passive discharge pulse. The invention is applicable to any type of multi-phase stimulation implementing the various pre-charge or post-charge, stimulation and passive discharge time phases, in particular neurostimulation. In the remainder of the document, reference is made to pre-charging, but the invention may be applied in similar manner to post-charging.

In any event, the pre-charge phase comprises applying a current pulse of opposite direction to the direction of current of the stimulation pulse, and of controlled amplitude and controlled duration, in order to produce a total charge $-Q$ equal but opposite to the charge Q of the stimulation.

To prevent the pre-charge from producing physiological effects, the amplitude of the pre-charge pulse is adjusted to a level that is much lower than the level of a simulation pulse, its duration or width being extended so that the corresponding quantity of charge (equal to the product of the current multiplied by the duration or width of the pulse) is of the same order of magnitude as the stimulation charge to be compensated. For example, a stimulation pulse of 3 mA/0.5 ms is compensated for by a pre-charge pulse of 0.5 mA/3 ms.

The aim of a stimulator producing such multi-phase pulse trains is to obtain the expected physiological effects, e.g. a reduction in heart rate, a controlled modification in the sympathovagal balance, etc. while also maintaining an overall balance of electric charges at the end of the pulse train. However, only the stimulation should produce a physiological effect, the compensatory phases (pre-charge, post-charge, passive discharge) should not be effective physiologically.

In such a situation, the main problem is to make sure that the compensatory phases (pre-charge(s) and passive discharge) do not produce undesirable physiological effects.

Unfortunately, nerves, in particular the vagus nerve, which is often the target of neurostimulation therapy, are made up of a very large number of nerve fibers of different types (types A, B, and C in particular for the vagus nerve), each type of fiber having its own characteristics as regards activation threshold and velocity of propagation of the nerve impulse. Thus, the thickest fibers have a low activation threshold and a high velocity of propagation, while the thinnest fibers have the reverse properties.

The compensatory phases can thus produce certain physiological effects due to the pulse being captured by certain nerve fibers, and potentially those that have the lowest excitation threshold. It is also necessary to take account of the fact that the fibers that are shallowest, close to the electrodes, receive more current than the same fibers that are situated deep in the nerve, and can therefore also be activated even if their excitation threshold is higher.

SUMMARY

A first object of the invention is thus to achieve capture during the stimulation phases in the fibers that are to be activated, while avoiding such capture during the compensatory phases.

Other unexpected effects can be observed on organs that are innervated by the stimulated nerve. Typically, it is known that the heart rate is slowed by stimulating the vagus nerve, but it is observed that additional slowing can be produced by the parasympathetic nerves (fibers of the B type) as excited by the compensatory phases. Multi-phase stimulation with pulse trains having stimulation phases and compensatory phases thus induces a large reduction in the heart rate, larger than what would be observed with mere mono-phase stimulation not including any compensatory phases.

A second object of the invention is thus to make it possible to evaluate and to control any physiological response produced by the compensatory phases.

Finally, every time neurostimulation is applied by the generator of the device, the device goes into an absolute refractory period during which disconnection or "blanking" of the sensing or detection circuits takes place, in particular blanking of the cardiac activity and of the electroneurogram, and it is only at the end of the blanking period that the sensing and measurement circuits for sensing and measuring the physiological potentials are reactivated.

A third object of the invention is to make it possible to minimize the durations of the compensatory phases (pre-charge, post-charge, and passive discharge), in such a manner as to reduce the blanking period accordingly and thereby enable the device to return rapidly to normal operation, i.e. with all of the functions for sensing or detecting the physiological potentials. However, it should be noted that if the duration or width of a pre-charge pulse is reduced, the amplitude needs to be increased by the same amount in order to keep the same electric charge value, that resulting in a risk of inducing physiological effects that would not have appeared with a pulse that is longer and of smaller amplitude.

In order to achieve the above-mentioned objects, the basic idea of the invention thus consists in providing a sensing circuit for detecting a physiological and/or physical parameter, and in producing a test pulse train so as to discriminate and evaluate the appearance of any physiological effect produced by the compensatory phases, and then in controlling the neurostimulation generator as a function of the result of the test in such a manner as to adapt the parameters of the active compensatory phase(s), i.e. the pre-charge or post-charge pulse(s), or indeed the passive discharge pulse(s).

The physiological and/or physical parameter may be a parameter of the electrical activity of the heart, e.g. the cardiac rhythm, i.e. the heart rate (HR), as computed on the basis of the RR (R-to-R) intervals of an endocardial electrogram EGM. It may also be a parameter of electrical activity of the nervous system, which parameter is derived from an electroneurogram (ENG) signal, or a parameter of respiratory rate (minute ventilation (MV)), of electric current flowing through a tissue, of acceleration of the body of the patient (acceleration (G)), of blood pressure, of endocardial acceleration EA, etc. In another embodiment, the active compensatory phase(s) may be adjusted to the level of the passive discharge, in order to balance out the charges.

Depending on the embodiment implemented and on the particular application, the test multi-phase pulse train may or may not include one or more stimulation pulses. In other words, depending on the situation, the test may be performed using neurostimulation pulses combined with pre-charge pulses, or merely using pre-charge pulses, without any neurostimulation.

The principle of the invention may be applied either to a system of single electrodes (in particular bipolar, quasi-tripolar, or tripolar), or to a system combining a plurality of stimulation electrodes (in particular multipolar). Finally, the invention is applicable to any biological stimulation system in which the stimulation is delivered in current (in particular myocardial or muscular stimulation).

More specifically, the invention provides an active medical device comprising, in a manner known per se and disclosed in particular by above-mentioned US2010/0114198 A1:

a generator for generating functional electrical neurostimulation, which generator comprises means for producing multi-phase neurostimulation pulse trains as output;

a stimulation lead, designed to be disposed on or in the vicinity of a structure of the nervous system of a patient wearing the device and for applying neurostimulation pulse trains to said structure;

at least one sensor delivering a monitoring signal representative of a physiological and/or physical parameter that can be influenced by the delivery of the neurostimulation pulse trains; and an automatic control circuit for automatically controlling charge compensation, which circuit comprises means for receiving as input the monitoring signal delivered by the at least one sensor;

In a manner characteristic of the invention, each pulse train comprises at least one stimulation pulse and at least one compensatory pulse, said at least one compensatory pulse comprising: a pre-charge pulse preceding the stimulation pulse; and/or a post-charge pulse following the stimulation pulse; and a passive discharge pulse terminating the pulse train; or a combination of the preceding pulses. The stimulation and compensatory pulses are current pulses in which the direction, the duration and the amplitude are controlled, and the compensatory pulses procure a cumulative electric charge that compensates for the electric charge of the at least one stimulation pulse.

In addition, the automatic control circuit for automatically controlling charge compensation further comprises means for determining an amplitude and/or a duration for a compensatory pulse as a function of at least one predetermined criterion, and means for delivering to the generator a control signal for controlling the compensatory pulses to be produced as output by said generator.

According to various advantageous subsidiary characteristics:

the automatic control circuit for automatically controlling charge compensation is a circuit suitable for: controlling the generator in such a manner as to produce at least one test pulse train; collecting the monitoring signal after the end of the at least one test pulse train; determining, based on the level of the monitoring signal, whether or not a physiological and/or physical effect is produced by applying the test pulse train; and determining the amplitude and/or the duration of the compensatory pulses of the following pulse trains as a function of the result of the determination;

the test pulse train comprises a pre-charge pulse followed by at least one stimulation pulse; in which case, the automatic control circuit for automatically controlling charge compensation is advantageously suitable for delivering a single test pulse train and means for collecting the monitoring signal immediately after the end of the test pulse train;

in a variant, the test pulse train comprises a pre-charge pulse but does not comprise stimulation pulse; in which case, the automatic control circuit for automatically controlling charge compensation is advantageously suitable for delivering a plurality of successive test pulse trains and means for collecting the monitoring signal after the end of the last test pulse train of said plurality;

the automatic control circuit for automatically controlling charge compensation is suitable for determining the amplitudes and/or the durations of the compensatory pulses of the current pulse trains as a function of the maximum amplitude of the passive discharge pulse measured for the test pulse train.

the automatic control circuit for automatically controlling charge compensation is also suitable for controlling a time interval between the end of the stimulation pulse and closure of switches for putting the stimulation electrodes at the same potential, in such a manner as to modulate the starting instant of the passive discharge pulse;

the automatic control circuit for automatically controlling charge compensation is also suitable for controlling a time interval between the end of the pre-charge pulse and the start of the stimulation pulse;

the automatic control circuit for automatically controlling charge compensation is also suitable for controlling a time interval between the closure and the opening of switches for putting the stimulation electrodes at the same potential, in such a manner as to modulate the duration of the passive discharge pulse;

the sensor is a sensor for measuring a parameter from the group formed by: electrical activity of the heart, electrical activity of the nervous system, heart rate, respiratory rate, electric current flowing through a tissue, acceleration of the patient's body, blood pressure, endocardial acceleration, position of the patient.

BRIEF DESCRIPTION OF THE DRAWINGS

An embodiment of the present invention is described below with reference to the accompanying drawings, in which like references designate identical or functionally similar elements from one figure to another, and in which:

FIGS. 8a and 8b are circuit diagrams showing the equivalent circuits of the pulse generator (for generating stimulation or pre-charge pulses) and the interface with the tissues receiving the pulses, respectively during a pulse application phase and during a passive discharge phase;

FIG. 9 is a representation in superposition, and characteristic of the invention, of the shape of a passive discharge, as superposed with a Lapicque diagram as shown in FIG. 7;

FIG. 15 is a flow chart showing the main steps of implementing the technique of the invention;

FIG. 16 shows application of two neurostimulation pulse trains delivered in synchronism with the heart rate;

DETAILED DESCRIPTION

An embodiment of the device of the invention is described below.

As regards its software aspects, the invention can be implemented by suitably programming the control software of a known stimulator, e.g. of the neurostimulator, myostimulator, cardiac stimulator (pacemaker), rescynchronizer and/or defibrillator type, comprising means for acquiring a signal supplied by endocardial leads and/or by one or more implanted sensors.

The invention may, in particular, be applied to implantable devices such as those belonging to the Equilia, Reply, and Paradym families of devices that are produced and sold by Sorin CRM, Clamart, France.

Such a device has a programmable microprocessor and comprises circuits for receiving, shaping, and processing the electrical signals collected by implanted electrodes, and for delivering stimulation pulses to said electrodes. It is possible to transmit software to it by telemetry, which software is kept in a memory and is executed for implementing the functions of the invention that are described below. Adapting such equipment to implementing the functions of the invention is within the capacities of the person skilled in the art, and is not described in detail.

The method of the invention is implemented by hardware and software means, using suitable algorithms executed by a microcontroller or a signal digital processor, and by using a current stimulation circuit. To make the description clearer, the various types of processing applied are broken down and represented diagrammatically by a certain number of distinct functional blocks shown in the form of interconnected circuits, but this representation is given merely by way of illustration, said circuits including common elements and corresponding, in practice, to a plurality of functions executed together by a common piece of software.

Figure 1:
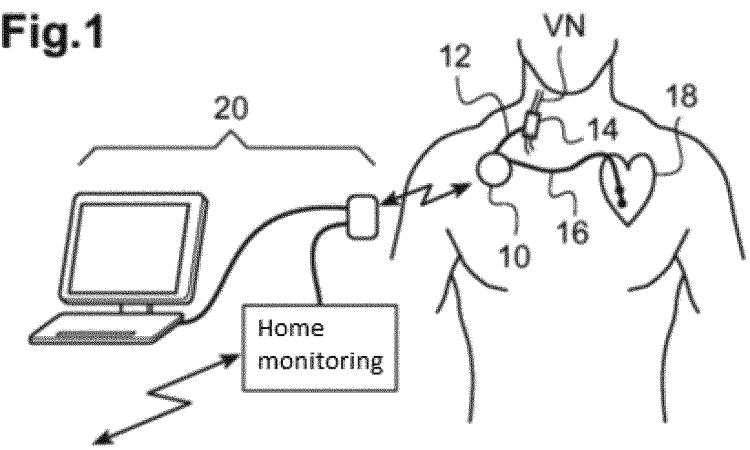
FIG. 1 is an overall view of a patient in whom a vagus nerve stimulation (VNS) device is implanted, which device comprises means for collecting the heart rate by means of an endocardial lead.

In FIG. 1, reference 10 designates the housing of an implantable generator for vagus nerve stimulation (VNS). The stimulation is delivered by a lead 12 that, at its distal end, carries a sleeve 14 implanted around the vagus nerve VN, said sleeve 14 being provided with electrodes that are suitable for stimulating the vagus nerve by applying bursts of VNS pulses produced by the generator 10. The generator 10 also comprises means for collecting the heart rate, which means are, in this example, constituted by an endocardial cardiac lead 16 provided at its distal end with electrodes 18 for sensing the electrical activity of the ventricle. This lead 16 thus collects endocardial electrogram (EGM) signals making it possible, at each cardiac cycle, to detect a ventricular depolarization wave R.

In other embodiments, the detected signal is a physiological signal, in particular the minute ventilation or the electroneurogram. In another embodiment, the active compensatory phase(s) may be adjusted to the level of the passive discharge, in order to balance out the charges.

Preferably, the VNS is applied to the right vagus nerve at the cervical level. In other embodiments, the VNS is applied on the left and/or on a branch of the vagus nerve. In yet other embodiments, the neurostimulation is applied in the vicinity of a nerve or one of its branches of the parasympathetic system.

The generator 10 may optionally be designed such that, in addition to delivering the neurostimulation pulses applied to the vagus nerve VN, it delivers cardiostimulation pulses applied to the electrodes 18 (and optionally to other ventricular or atrial electrodes) for treating bradycardia, tachycardia, or ventricular synchronization disorders. However, this function is not necessary for implementing the invention, which relates only to neurostimulation therapy and to analyzing the effects of that therapy, particularly (but not necessarily) on the basis of cardiac signals collected by endocardial electrodes, which may be used equally well as mere signal detection electrodes or as combined detection/stimulation electrodes.

The overall device may also be provided with a communications system 20 comprising an external telemetry housing or box making it possible to communicate with the generator 10 for transferring data thereto and for receiving data therefrom. The communications housing may also be connected to an external device such as a programmer, or indeed a home monitoring device for remotely monitoring the patient through the data collected and recorded by the generator being transmitted to a remote site.

It should also be noted that, in the example shown, the technique of the invention is based mainly or exclusively on analyzing cardiac signals (EGM signals in this example) for analyzing the physiological effect of the neurostimulation and for adjusting the operating parameters of the generator 10. However, in a variant or in addition, this analysis may be based on signals produced by sensors relative to other physical or physiological parameters such as: electrical activity of the nervous system (by analyzing an electroneurogram ENG), respiratory rate (in particular the minute ventilation signal MV), electric current flowing through a tissue, acceleration of the patient's body (information given by an accelerometer incorporated into the implanted generator), blood pressure, endocardial acceleration EA (by an acceleration sensor incorporated into the cardiac lead 16), etc. In general, the idea is to have a signal representative of at least one physiological or physical parameter that can be influenced by delivery of stimulation pulses, and in this example by delivery of VNS pulses.

Figure 2:
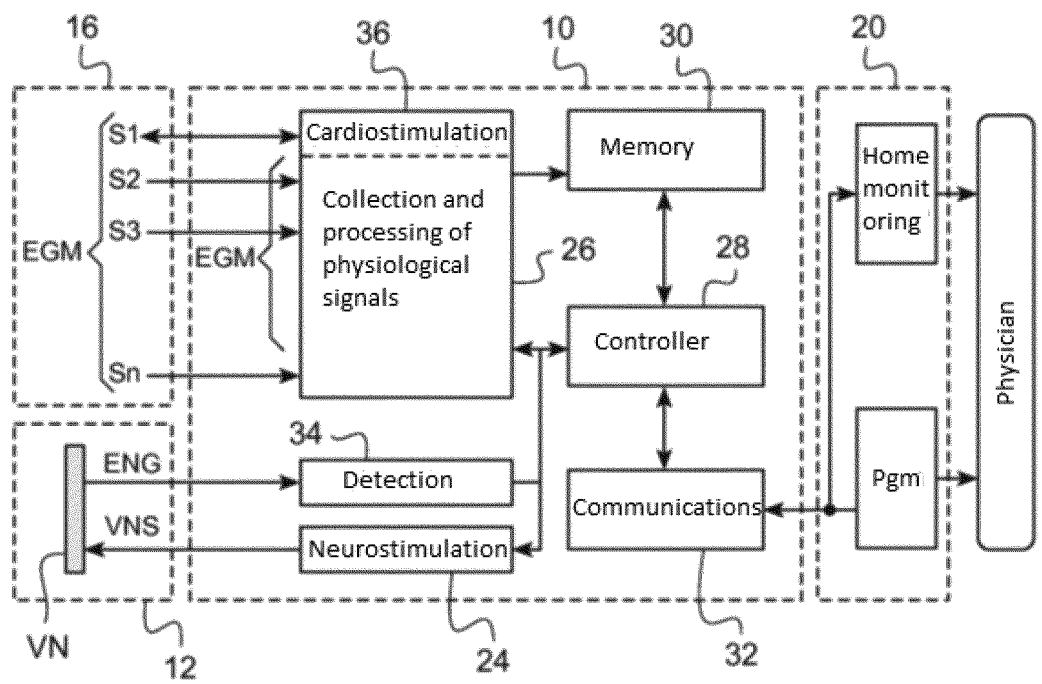
FIG. 2 diagrammatically shows the main functional blocks of the generator of the VNS device of FIG. 1 for implementing the invention.

FIG. 2 is an overall view of the various functional blocks of the generator 10 of FIG. 1 making it possible to implement the invention, with the input and output signals.

The generator 10 comprises a circuit 24 for producing VNS pulses, which are current pulses in which i) the direction (i.e. sign), ii) the amplitude of the current, and iii) the duration (pulse width PW) are controlled as a function of predetermined parameters. These pulses are applied to the vagus nerve VN by the lead 12, in the manner described above.

In another application, the configuration of the stimulation poles may be programmable, in particular in a multi-polar device having a plurality of electrical contacts.

The generator 10 also comprises a circuit 26 for collecting and processing physiological and/or physical signals, which, in this example, are signals of the electrical activity of the heart that are delivered by one or more electrodes of the endocardial lead 16 (endocardial electrogram signals EGM) collected on one or more channels S1 . . . Sn. As indicated above, this circuit can also collect other signals such as: electroneurogram ENG, endocardial acceleration EA, respiratory activity (MV signal), acceleration of the patient's body (G signal), peak level of the passive discharge, etc.

The circuits 24 and 26 are interfaced to a controller 28 and to a memory 30, in particular so as to enable the neurostimulation circuit 24 to be controlled, in the manner described below, as a function of the physiological and/or physical signals collected by the circuit 26.

The generator may, as indicated above, also comprises a communications interface 32 for exchanging data with external devices 20, such as a programmer, so as to make interaction possible with a physician close to the patient, and/or with a home monitoring device for transmitting data to a remote site where said data is analyzed.

The generator 10 may also comprise a circuit 34 for detecting nervous activity signals (electroneurogram ENG), in particular signals collected by the electrodes of the sleeve 14 in contact with the vagus nerve VN.

Finally, the generator 10 may, where applicable be provided with a cardiostimulation circuit 36 suitable for delivering anti-bradycardia, anti-tachycardia and/or ventricular resynchronization therapy pulses.

The type of pulses produced by the neurostimulation circuit 24 is explained below with reference to FIGS. 3 and 4.

Figure 3:
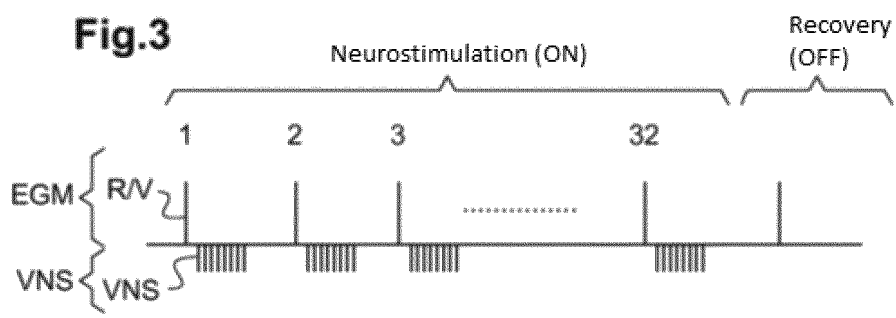
FIG. 3 shows a sequence of delivery for delivering VNS therapy pulse trains that are synchronized on detection of heart beats.

FIG. 3 shows a sequence of delivering VNS therapy pulse trains that are synchronized on detection of the heat beats, and more specifically on detection, by the circuit 26, of a ventricular depolarization that may be stimulated (V event) or spontaneous (R event).

Typically, the VNS pulse bursts are delivered during "ON" periods of predetermined duration, interspersed with "OFF" periods during which no VNS stimulation is delivered. Such VNS stimulation bursts, controlled by the controller 28, may be defined by numerous configuration parameters such as:

synchronism: the VNS stimulation may be synchronous (as in this example) or not synchronous with the cardiac events;

when stimulation is synchronous, ratio between the VNS stimulations and the cardiac events, a ratio of 1:1 indicating a VNS stimulation at each detected cardiac event, a ratio of 1:4 indicating a VNS stimulation every four cardiac events, etc.;

also when stimulation is synchronous, duration of the R-VNS interval, a parameter describing the delay between detection of the cardiac event and the start of the burst of VNS pulses, number of VNS pulses in the burst;

current delivered to the vagus nerve (peak current or mean current);

frequency of the pulses;

width of the pulses; and duty cycle between the stimulation "ON" periods and the non-stimulation "OFF" periods.

As indicated in the introduction, the invention relates specifically to when the stimulation is applied in the form of a succession of multi-phase pulse trains, each of which comprises:

a least one pre-charge pulse (and/or post-charge pulse, considered herein to constitute a situation similar to that of a pre-charge pulse), delivered in controlled manner by the generator 24;

at least one neurostimulation pulse proper, also delivered by the neurostimulation circuit 24; and a pulse appearing in the form of a spontaneous, passive discharge, in the bioimpedance formed by the tissues at the stimulation site.

The stimulation pulse is delivered in the form of a current of predetermined direction (i.e. of predetermined sign), and constitutes a "stimulation phase", while the pre-charge pulses are in the form of a current of opposite direction (i.e. of opposite sign), corresponding to a "compensatory phase". The passive discharge is applied after the pre-charge, stimulation, and post-charge pulses. Theoretically, the cumulative (total) electric charge of the compensatory phase(s) is equal, ignoring the sign, to the electric charge of the stimulation pulse.

Figure 4:
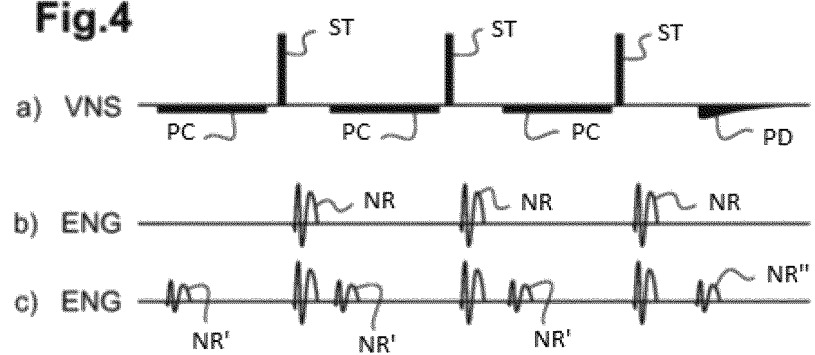
FIG. 4 shows more specifically an example of a neurostimulation pulse train, with the desired effects on the electroneurogram (ENG) but also the undesirable effects produced by each of the pulses of said pulse train.

FIG. 4 shows at (a) an example of a neurostimulation multi-phase pulse train, with three stimulation pulses ST, each of which is preceded by a pre-charge pulse PC, the pulse train ending with a passive discharge pulse DP.

As described in the introduction, the pre-charge pulse PC (which may also be a post-charge pulse produced after the stimulation pulse ST) is a pulse of direction (direction of the delivered current) opposite to the direction of the neurostimulation pulse ST, and delivers to the tissues a quantity of charge approximately equal to that of the stimulation pulse ST, in such a manner as to procure final electrical neutrality and avoid excessive accumulation of charges at the interface for stimulating the vagus nerve. At the end of the pulse train, the passive discharge DP corresponds to removing any residual charges still present at the stimulation site.

The polarity of the passive discharge DP is, a priori, not known, because it depends on the residual charges at the electrodes-tissues interface. Consideration must be given to two phenomena: 1) the inaccuracy inherent to any system does not make it possible to balance the delivered charges, in absolute terms, of the stimulation pulse and the charges of the pre-charges and post-charges; and 2) some charges might have dissipated into the ambient environment.

At (b) and (c), electroneurogram ENG plots show:

the desired effects NR on the nervous system, which effects result from the stimulation pulse proper ST, and are visible at b);

but also, as can be seen at (c), the undesirable effects NR' and/or NR" produced respectively by the pre-charge pulses PC and by the passive discharge PD.

An object of the invention is to propose a technique making it possible to control these unexpected neural responses NR' and NR", generally to attempt to make them disappear by suitably parameterizing the pre-charge pulses PC.

In a variant, instead of seeking to reduce or to eliminate such unexpected responses, it is endeavored to control such responses on the nervous system that are produced by the compensatory phase of the neurostimulation, in such a manner as to control the overall response produced both by the pre-charge pulses PC and by the stimulation pulses ST.

Figure 5:
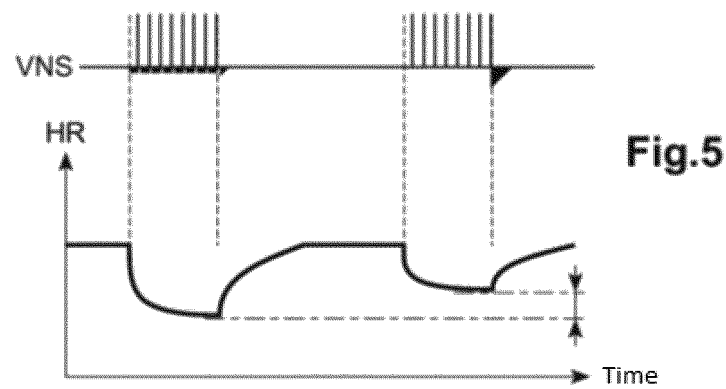
FIG. 5 shows an example of an effect produced on the heart rate by neurostimulation pulse trains, respectively with and without a pre-charge pulse.

FIG. 5 shows an example of an effect produced on the heart rate by neurostimulation pulse trains, with a first train containing pre-charge compensatory pulses and the second train in which such pre-charge compensatory pulses have not been applied.

The second timing diagram shows that the pre-charge pulses produce an additional reduction in the heart rate HR (i.e. a lengthening of the RR time lapse between two successive cardiac cycles, relative to a pulse train with no pre-charge pulse).

This phenomenon is due to the capture of parasympathetic fibers, in particular the fibers of the A type and/or of the B type of the vagus nerve, acting on the heart rate via the compensatory phases. In such a situation, an effect of using pre-charge compensatory pulses is to amplify the physiological effect produced by the neurostimulation, a phenomenon that needs to be taken into account for adjusting the parameters of the neurostimulation.

Figure 6:
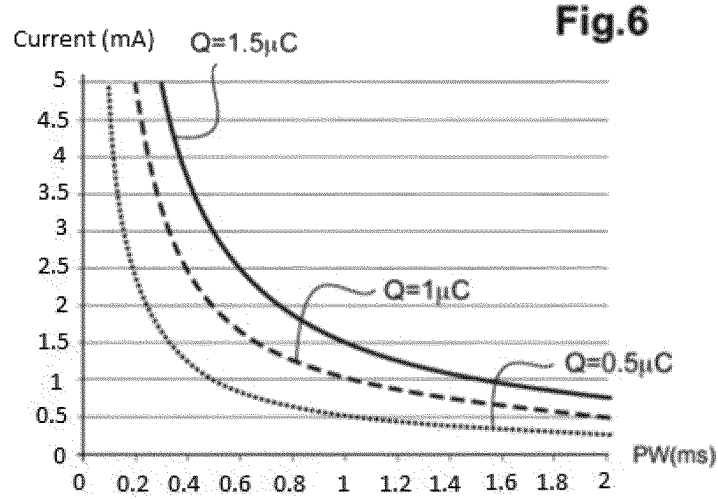
FIG. 6 shows an "iso-charge" characteristic curve, for three charge values produced by a current pulse as a function of the duration or pulse width (PW) of said pulse.

FIG. 6 is a representation of an "iso-charge" characteristic curve showing the relationship between the duration or width PW of the pulse and the magnitude of the current, at constant charge, for three different charge values $Q=0.5$ μC, $Q=1$ μC, and $Q=1.5$ μC produced by a current pulse. Since the charge is the product of the duration of the pulse (which is assumed to be rectangular) multiplied by the current, said curves are in the form of hyperbolas.

Thus, a stimulation pulse of 1 ms/1 mA, i.e. 1 μC, can be compensated for by a pre-charge pulse of 2 ms/0.5 mA, or of 3 ms/0.33 mA, or of 4 ms/0.25 mA, or of 5 ms/0.20 mA, or of 6 ms/0.17 mA, etc. Naturally, in order to minimize or cancel out the physiological effects produced by the pre-charge pulse, it is sought to lengthen said pre-charge pulse to a pulse width value that makes it possible to reduce accordingly the amplitude of the compensatory current, and thus the unwanted physiological effects attached to said pulse.

Figure 7:
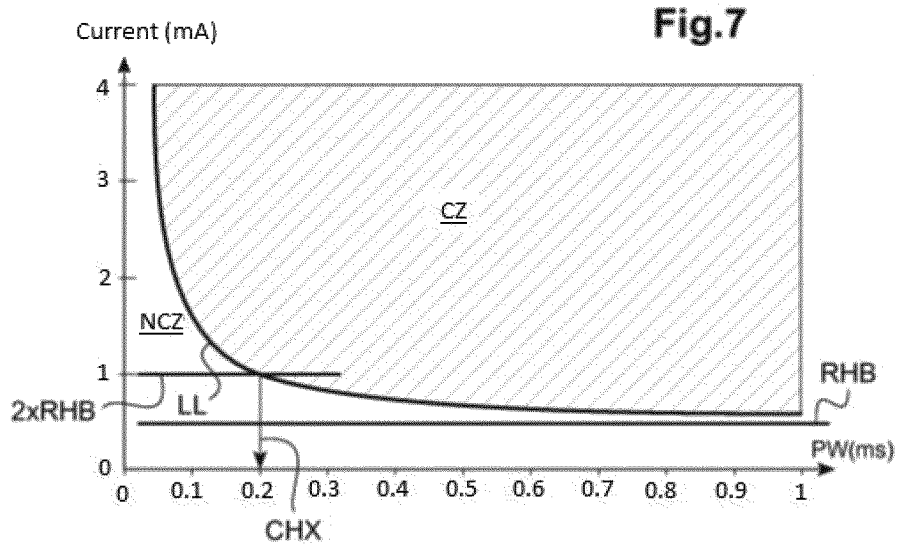
FIG. 7 is a Lapicque diagram describing the relationship between the characteristics of a stimulation pulse and a resulting physiological response.

FIG. 7 is a representation, in a current/pulse width space, of the "Lapicque's Law" diagram that describes the relationship between the characteristics of current and of pulse width of a pulse, and the physiological response induced (or not induced) by said pulse.

When the physiological response is a cardiac parameter such as heart rate HR, the physiological response is of the "all or nothing" or "on/off" type, i.e. depending on the situation, the pulse produces either complete depolarization of the heart (capture zone CZ), or complete absence of depolarization (non-capture zone NCZ). The border between the two zones CZ end NCZ, i.e. the lower boundary of the capture zone CZ is the "Lapicque's Law" characteristic curve LL.

The Lapicque curve is typically characterized by two descriptors, namely:

plotted up the axis of ordinates, the current referred to as the "rheobase" RHB, which is the current level at which no capture is ever possible regardless of the widths of the pulses (horizontal asymptote of the curve LL); and plotted along the axis of abscissas, a duration referred to as "chronaxie" CHX, which is the pulse duration or width corresponding, by convention, to twice the rheobase RHB.

FIGS. 8a and 8b are circuit diagrams showing the equivalent circuits of the pulse generator (for generating stimulation pulses ST or pre-charge pulses PC) and the interface with the tissues receiving the pulses, respectively during a pulse application phase and during a passive discharge phase.

In a phase of application of a pulse (FIG. 8a), the generator produces a current I in one direction or the other (depending on whether the pulse is a pre-charge pulse or a stimulation pulse), which current is applied to the interface, represented typically by a bioimpedance BZ comprising a capacitor C with a parallel resistor R and a series resistor r. Said bioimpedance BZ is coupled to the generator by a link capacitor $C_t$.

During the passive discharge (FIG. 8b), which follows application of the neurostimulation pulse or pulses, the stimulation electrodes are put at the same electric potential (switches SW and SW of equivalent resistance R and R', typically but not exclusively connected to ground) and the charge accumulated in the link capacitor $C_t$ produces a potential difference that causes a current to flow in a loop constituted by the bioimpedance BZ, the link capacitor $C_t$ and the internal resistors R and R' of the switches SW and SW. The current decreases progressively, in accordance with a relationship for discharge of a capacitor in a complex impedance comprising both capacitive and resistive components.

Basic Principles of the Invention

The starting point of the invention lies in a superposition of an iso-charge curve (as in FIG. 6) and of a curve of the Lapicque's Law type (as in FIG. 7), which curves have the same magnitudes on the axis of abscissas and on axis of ordinates, namely the pulse widths PW and the currents.

Figure 14:
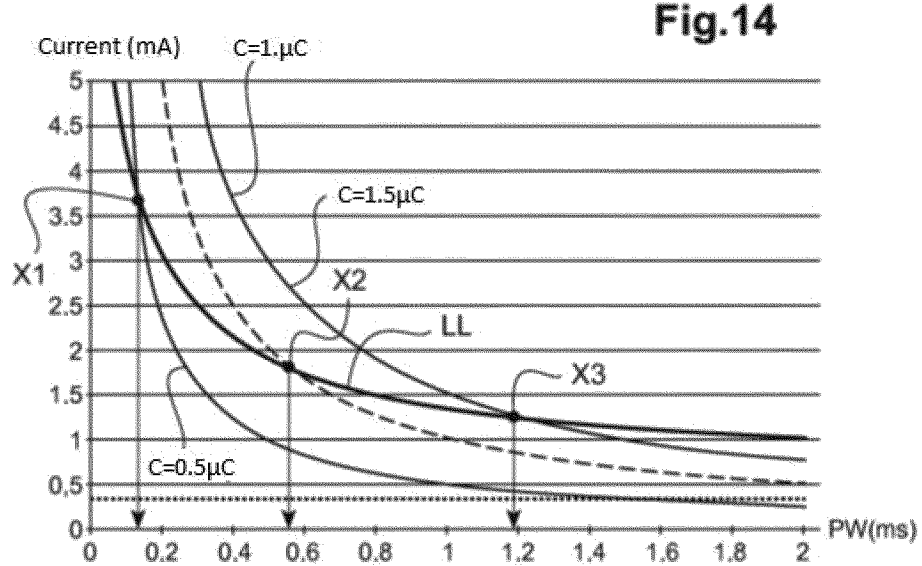
FIG. 14 shows the iso-charge characteristic curves determined for various charge values produced by the passive discharge pulse of a compensatory phase, in superposition with a characteristic curve according to Lapicque's Law.

FIG. 14, described in detail below, shows such a representation with the Lapicque's Law curve LL being superposed with several iso-charge characteristic curves.

A second aspect of the invention consists in taking into account the effects of a passive discharge on the tissues by mutually superposing a Lapicque curve and a passive discharge curve, which curves have the same magnitudes on the axis of abscissas and on the axis of ordinates, namely the pulse widths PW and the currents.

FIG. 9 shows the parameters of a pulse of duration $PW_P$ and of current $I_P$ corresponding to an equivalent of a passive discharge DCH. In practice, the passive discharge takes place in a negative exponential pattern, corresponding to discharging of the tissues-electrodes interface and of the link capacitors (to a first approximation equivalent to the discharge of a capacitor into a resistor).

In the example shown, the DCH curve corresponding to a passive discharge is always above the area corresponding to the $\{PW_P, I_P\}$ pulse, which means that the biological effects of the passive discharge are always as large as the biological effects of the pulse. In addition, the point ST corresponding to the $\{PW_P, I_P\}$ pulse is situated significantly above the curve corresponding to Lapicque's Law LL, which means that said pulse does indeed produce a stimulation (since the point ST is situated in the capture zone CZ). It can thus be concluded, in this example, that, relative to the Lapicque's Law curve LL, the passive discharge also produces a stimulation physiological effect.

The hatched zone Z1 indicates a zone that should necessarily be avoided by the passive discharge, because said passive discharge could excite nervous fibers and thus produce an undesirable physiological effect.

An object of the invention is to propose a technique making it possible to adjust the characteristics of the pre-charge (or post-charge) pulse in such a manner as to control the maximum level of the passive discharge pulse, typically so as to minimize it below the stimulation threshold, or indeed to make it almost disappear, by optimum balancing of the quantity of charge of the pre-charge pulse relative to the stimulation pulse.

Figure 10A:
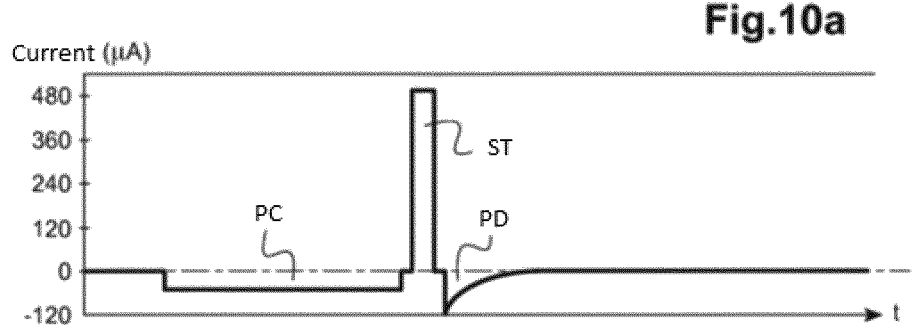
FIGS. 10a, 10b, and 10c show three examples of a multi-phase pulse train with, for the same stimulation pulse, pre-charge pulses of different amplitude or of different duration, generating passive discharge pulses of different levels.
Figure 10B:
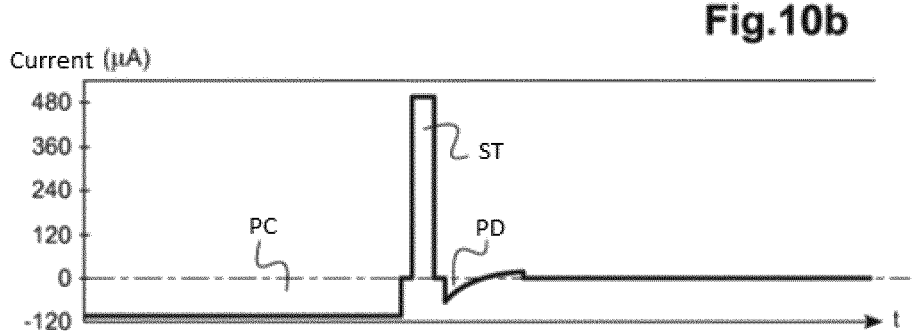
Figure 10C:
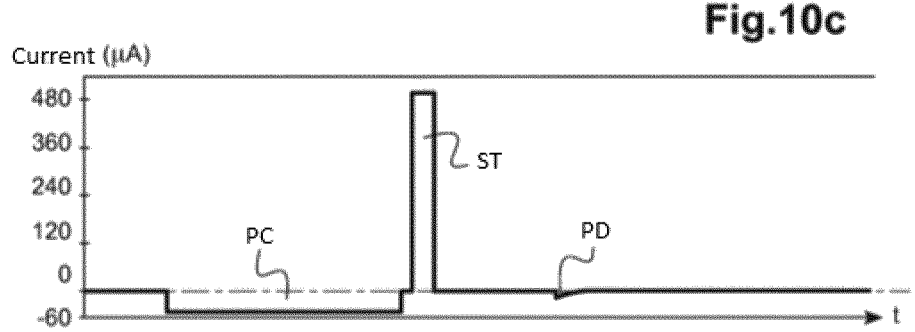

FIGS. 10a, 10b, and 10c show three examples of a multi-phase pulse train, each example having the same stimulation pulse ST, but having respective pre-charge pulses PC of different amplitudes or of different durations, generating passive discharge pulses PD of different levels and of different configurations.

In all three figures, the stimulation pulse ST is a pulse of 0.5 mA/300 microseconds (µs).

In FIG. 10a, a pre-charge pulse PC of −50 µA/3 ms is generated that corresponds to a charge value equal, ignoring the sign, to the charge value of the stimulation pulse, and thus to a pre-charge that, a priori, is balanced.

In this situation, it is observed that a passive discharge PD appears for which the initial edge produces a current peak of about −110 µA, i.e. more than twice the value of the pre-charge current (−50 µA). Said passive discharge pulse is thus very likely to produce an undesirable physiological effect.

Said discharge is a passive capacitive discharge that is not controlled per se, and that actually depends only on the level of the charges applied to the interface with the nerve, on the bioimpedance thereof, etc.

The basic idea underling the invention thus consists in modulating the amplitude and/or the duration (width) of the pre-charge pulse PC, thus the value of the charge applied prior to the stimulation, in such a manner as to act indirectly on the level of the current peak of the passive discharge PD, whenever it is observed that the applied pre-charge has an effect on the level of the passive discharge pulse PD.

Thus, in FIG. 10b, a pre-charge pulse PC of −100 µA/4 ms is generated that is thus, a priori, not balanced relative to the stimulation pulse ST, which is still 0.5 mA/300 µs. However, in this situation, a considerable reduction in the peak of the passive discharge PD is observed, with an initial edge of only about −65 µA, less than the level of the pre-charge pulse (−110 µA) and half what is observed (−110 µA) with a balanced pre-charge pulse (situation of FIG. 10a).

Thus, by modulating the pre-charge pulse PC, it is possible to control the passive discharge PD to bring it to a level at which it does not produce any undesirable physiological effects, or any negligible effects.

Other sequencing for the pre-charge pulse PC may be considered for reducing the amplitude of the passive discharge PD, e.g. by modulating:
  the sequencing between the end of the pre-charge pulse PC and the start of the stimulation pulse ST;
  the sequencing between the end of the stimulation pulse ST and the start of the passive discharge pulse PD (this instant is controllable, because it corresponds to closure of the switches for putting the stimulation electrodes at the same electric potential);
  the sequencing between the start and the end of the passive discharge pulse PD (interval between closure and opening of the switches for putting the stimulation electrodes at the same electric potential).

As shown in the example of FIG. 10c, it is even possible to reduce the discharge pulse to almost zero: in this example, the same, balanced, pre-charge pulse is used as in FIG. 10a (namely a pre-charge pulse of −50 µA/3 µs), but the time lapse between the end of the stimulation pulse ST and the start of the passive discharge PD is extended to a value of about 1.6 ms instead of 0.1 ms as in FIGS. 10a and 10b. It is observed that this parameterization makes it possible to make the passive discharge pulse PD almost disappear.

Clinical Implementation of the Invention

Some examples of clinical implementations of the invention are described below with reference to FIGS. 11 to 26.

A first clinical application is to controlling heart rate.

Figure 11:
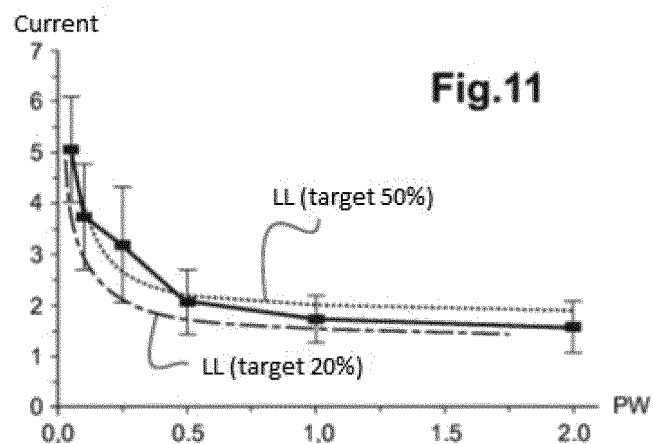
FIG. 11, in the context of applying the technique of the invention to controlling the heart rate, shows Lapicque's Law modeling for a given heart rate reduction target.

FIG. 11, in the context of such an application, shows Lapicque's Law modeling for a given heart rate reduction target. As indicated in the introduction, the heart rate HR is under the control of the autonomic nervous system, the sympathetic system acting by increasing the heart rate and the parasympathetic system (to which the vagus nerve belongs) acting by slowing the heart rate down.

By increasing the charge of the neurostimulation pulse delivered to the vagus nerve (current and pulse width), it is possible to act on the variations in the heart rate HR by suitably choosing VNS parameters (in particular current and pulse width). However, unlike with direct cardiac stimulation, i.e. applying depolarization pulses to endocardial electrodes, the effects on reduction of heart rate HR with neurostimulation are progressive effects, so that in such a situation the Lapicque's Law curve does not follow a model of the "all-or-nothing" type as described above, in particular with reference to FIG. 7.

The expected physiological response must therefore be quantified, e.g. a 20% reduction in heart rate, this expected response constituting a heart rate target that can be modeled, as shown in FIG. 11, in the form of a {pulse width, current} characteristic curve of the Lapicque's Law LL type. For a domain situated above this curve, the reduction in heart rate is greater than 20%, while for a point situated below said curve, said reduction is less than 20%. This limit defines a target physiological criterion.

For a lower target, e.g. a 10% reduction in heart rate, the Lapicque's curve LL' is situated in a lower region of the {pulse width, current} space.

Figure 12:
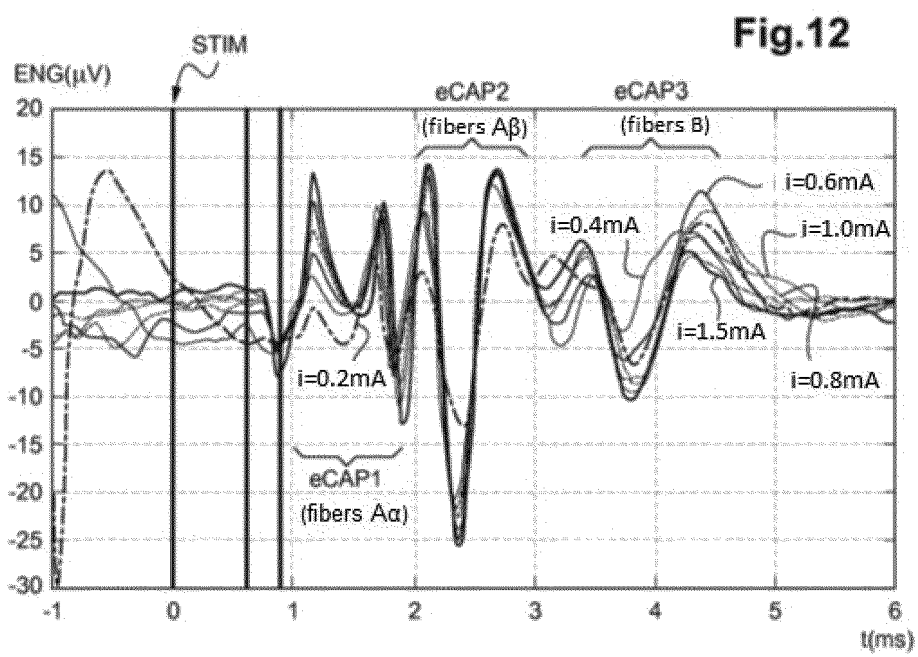
FIG. 12 is a neurogram showing the variations in the composite action potential for various values of the stimulation current.
Figure 13:
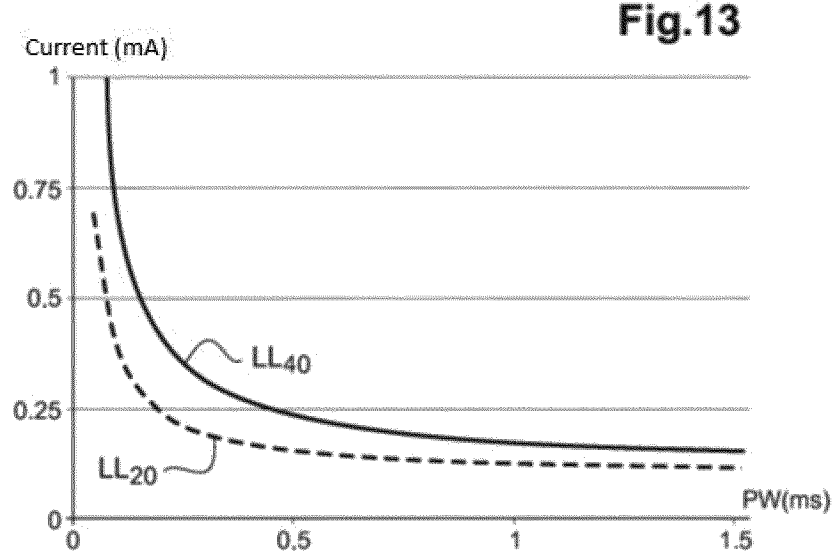
FIG. 13 shows characteristic curves according to Lapicque's Law, corresponding to different heart rate reduction targets.

A second clinical application, described with reference to FIGS. 12 and 13, is an application to controlled activation of a nerve fiber.

As indicated in the introduction, a nerve is made up of several thousand axons, the vagus nerve comprising more than 100,000 fibers. The fibers have a variety of diameters (ranging from 25 µm to 0.2 µm for the smallest fibers), and they may or may not be myelinated. They all lead to action potentials, but the conduction velocity depends on their diameter (the thickest fibers conduct the action potentials faster) and on whether or not they are myelinated (myelinated fibers conduct the action potentials faster). In addition, their stimulation threshold also depends on the same parameters (the thickest fibers and the myelinated fibers have lower activation thresholds, i.e. they are more readily excitable).

If a sufficient electrical stimulus is delivered to the nerve, said stimulus produces an evoked compound action potential (eCAP) that is the spatial sum of all of the action potentials produced by the fibers excited by the stimulus. In view of the diversity of the fibers, the fastest fibers (the thickest ones) produce action potentials as of the start of the eCAP, while the slowest fibers (the smallest-diameter ones) produce action potentials at the end of the eCAP. In addition, insofar as the activation threshold of a fiber, in terms of electric charge, depends on its diameter (the larger the diameter, the lower the activation threshold, and vice versa), the more the level of the stimulus increases the higher the number of activated fibers, so that the eCAP increases, in amplitude for fibers of the same type, and in duration for fibers having different characteristics.

FIG. 12 thus shows an example of an electroneurogram ENG showing the modifications of the evoked compound action potential for various levels of stimulus corresponding to currents lying in the range 0.2 mA to 1.5 mA. Thus, in FIG. 12, several components of the eCAP are observable, the Aα, Aβ, and B fibers (from the fastest to the slowest) appearing more or less close to the stimulation of the nerve.

As with controlling the heart rate, activating a nerve (eCAP) may be represented by a Lapicque curve, for a quantified target value. In this situation, the target value is expressed as a percentage of a component of the eCAP relative to its maximum value. In an implementation, the maximum value is the value measured by a system for collecting the ENG. In another implementation, it is a predefined typical value. For example, for the B fibers, if the measured maximum is 20 µV peak-to-peak, a target of 20% corresponds to an eCAP of B fibers equal to 4 µV. Similarly, for a typical value of 15 V, a target of 20% corresponds to a target of 3 µV.

Thus, FIG. 13 shows two examples of Lapicque's Law characteristic curves $LL_{20}$ and $LL_{40}$, respectively for the values of 20% and 40% of the maximum value for activating a defined potential. These values are given by way of example, and different values may be used in specific situations.

Prior Test for Determining the Optimum Compensatory Phase

Various algorithmic techniques are described below that make it possible, in accordance with the invention, to determine the parameters of amplitude and/or of duration (width) of the pre-charge pulse produced by the generator of the implanted device, for minimizing or indeed eliminating the undesirable side effects produced by the compensatory phase of the multi-phase stimulation.

FIG. 14 shows iso-charge characteristic curves for various charge values (C=0.5 µC, 1 µC or 1.5 µC) produced by a compensation phase of the multi-phase neurostimulation, in superposition with the Lapicque's Law characteristic curve LL corresponding to the desired target for the desired physiological effect, depending on the situation ("all or nothing" target, or else target quantified as a percentage as described above in the clinical application examples).

The intersection X1, X2 or X3 of the two curves (iso-charge and Lapicque's Law) corresponds to a "pivot point" that should be determined in order to adjust the characteristics of the compensatory phase, and in particular of the pre-charge pulse, as explained above with reference to FIG. 9.

FIG. 15 shows a general flow chart of the main steps in implementing the test making it possible to determine the charge of the compensatory phase $C_{pc}$ as a function of the stimulation charge $C_{ap}$ applied (in which the current and pulse width parameters are predetermined, be they set by the physician or computed by a specific algorithm).

The first step (block 100) consists in checking that the initial conditions for implementing the algorithm are all satisfied. These conditions may, in particular be:
time range predetermined (e.g. a time range chosen to be always the same);
patient has been at rest for a predetermined minimum time (condition checked on the basis of the signal produced by an activity sensor such as an accelerometer incorporated into the implanted device);
absence of application of a therapy for a predetermined time;
heart rate less than the maximum limit; and
rate (rhythm) regular, in particular absence of any acceleration or slowing of the RR intervals.

The following step (block 102) consists in setting a given compensatory charge level, which may be a level equal to the stimulation pulse charge, or may also depend on other parameters, such as heart rate, configuration of the electrodes, etc.

The device may, in particular, on the basis of the charge level set in this way, determine a series of {pulse width, current} pairs of values corresponding to said charge value. For example, for a predetermined charge $C_{pc}$=1 µC, the following table of pulse width values with their associated current levels is determined.

TABLE 1

| Index No. | PW (µs) | Current (mA) |
| --- | --- | --- |
| 1 | 500 | 2.00 |
| 2 | 600 | 1.67 |
| 3 | 700 | 1.43 |
| 4 | 800 | 1.25 |
| 5 | 900 | 1.11 |
| 6 | 1000 | 1.00 |
| 7 | 1100 | 0.91 |
| 8 | 1200 | 0.83 |
| 9 | 1300 | 0.77 |
| 10 | 1400 | 0.71 |
| 11 | 1500 | 0.67 |
| 12 | 1600 | 0.63 |
| 13 | 1700 | 0.59 |
| 14 | 1800 | 0.56 |
| 15 | 1900 | 0.53 |
| 16 | 2000 | 0.50 |
| 17 | 2100 | 0.48 |
| 18 | 2200 | 0.45 |
| 19 | 2300 | 0.43 |
| 20 | 2400 | 0.42 |
| 21 | 2500 | 0.40 |
| 22 | 2600 | 0.38 |
| 23 | 2700 | 0.37 |
| 24 | 2800 | 0.36 |
| 25 | 2900 | 0.34 |
| 26 | 3000 | 0.33 |
| 27 | 3100 | 0.32 |
| 28 | 3200 | 0.31 |
| 29 | 3300 | 0.30 |
| 30 | 3400 | 0.29 |
| 31 | 3500 | 0.29 |
| 32 | 3600 | 0.28 |

The following step (block 104) consists in applying a test neurostimulation sequence by scanning the various possible {pulse width, current} values by repeated simulations, with, in each case, measurement of the physiological and/or physical parameter that can be influenced by delivering the pulse (block 106). If necessary, the charge value that was established in 102 is then readjusted at the end of the scanning (block 108), the preceding process then be reiterated.

In an implementation, the system comprises only a system of bipolar or quasi-tripolar electrodes. In another implementation, it comprises a plurality of electrodes making stimulation possible on a plurality of dipoles or configurations of electrodes. The algorithm is then applied to each system of electrodes.

In an implementation, the algorithm of FIG. 15 is applied automatically by the stimulator without any external intervention. In another implementation, it is applied under the control of the physician, through the communications system, and makes it possible to set the values for the stimulation pulses and for the compensatory pulses. In another implementation, some of the functions are performed by the stimulator, and some of them are performed by the physician through the communications system.

Figure 17:
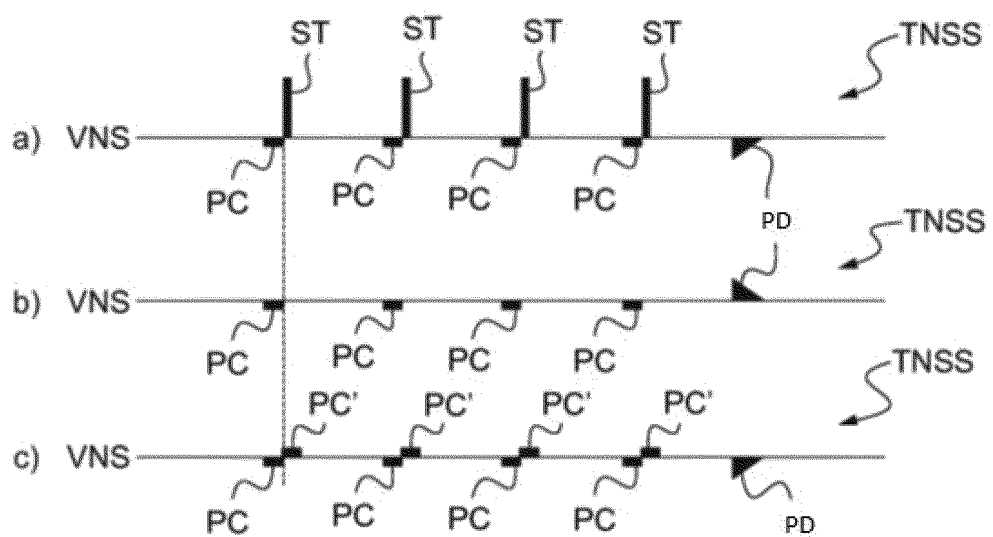
FIG. 17 shows application of three VNS modalities, of a neurostimulation multi-phase pulse train or of a test sequence where the pulse trains applied have different compensatory phase patterns.
Figure 18:
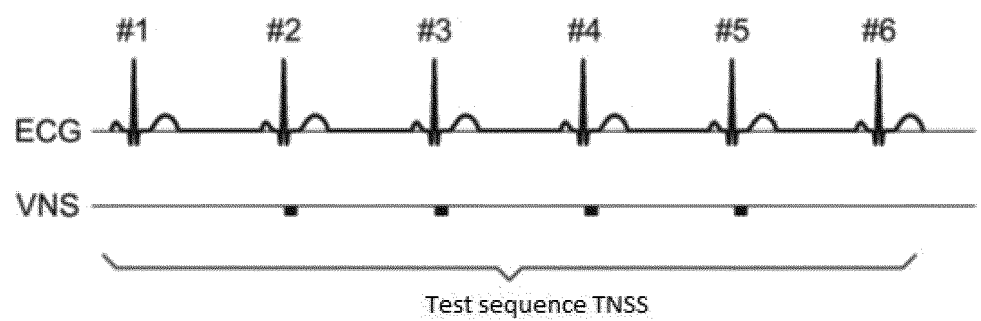
FIG. 18 shows a full test sequence, delivered in synchronism with the heart rate.

FIGS. 16 to 18 show more specifically how the multi-phase pulse trains of the test sequence are applied.

FIG. 16 shows application of two neurostimulation multi-phase pulse trains VNS delivered in synchronism with the heart rate EGM. The pulses may be delivered synchronously with the parasympathetic structure, but preferably they are delivered in a manner synchronized on the cardiac events, as shown in FIG. 16: the neurostimulation pulse train is then delivered in a manner synchronized on the P or R wave, with a time lapse TL between the detection of the P or R wave and the start of the neurostimulation pulse train.

FIG. 17 shows application of pulse train for a test neurostimulation sequence TNSS in which the applied pulse trains have different compensatory phase patterns:

at a), the test sequence comprises a predetermined number of pre-charge pulses PC associated with as many stimulation pulses ST. For example, the test sequence TNSS comprises four stimulation phases, each of which is preceded by a pre-charge pulse;

in the variant shown at b), only pre-charge pulses are applied in the test sequence TNSS;

in yet another variant, shown at c), the stimulation pulse is replaced by a pulse PC' identical to the pre-charge pulse PC but of reverse polarity, in such a manner as to prevent, at the end of the test sequence TNSS, electric charges from accumulating at the interface between the electrode and the physiological tissues.

As shown in FIG. 18, the full test sequence TNSS comprises a succession of stimulation bursts (as shown in FIG. 17) applied to consecutive cardiac events, e.g. the cardiac cycles No. 2 to No. 5 (#2 to #5), this test sequence being preceded (cycle No. 1) and followed (cycled No. 6) by cardiac cycles without any neurostimulation.

Iterative Search for Optimum Parameters for the Compensatory Phase

Some algorithmic techniques are described below with reference to FIGS. 19 to 26, these techniques making it possible scan the {pulse width, current} pairs in step 104 to find, in as little time as possible, the pivot point X that makes it possible to determine the best parameters for amplitude and/or duration to give to the pre-charge pulse, so as to minimize or indeed eliminate the undesirable side effects produced by the compensatory phase of the multi-phase stimulation.

Figure 19:
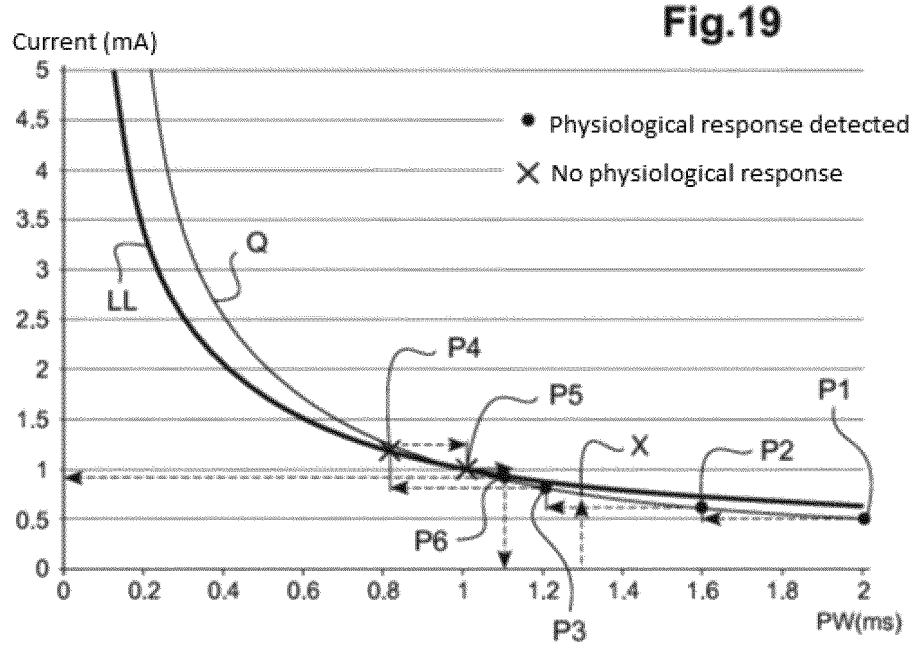
FIG. 19, on a superposition of the iso-charge characteristic curve and of the Lapicque diagram, shows a search technique for seeking the optimum point by using an algorithm of the iterative type.
Figure 20:
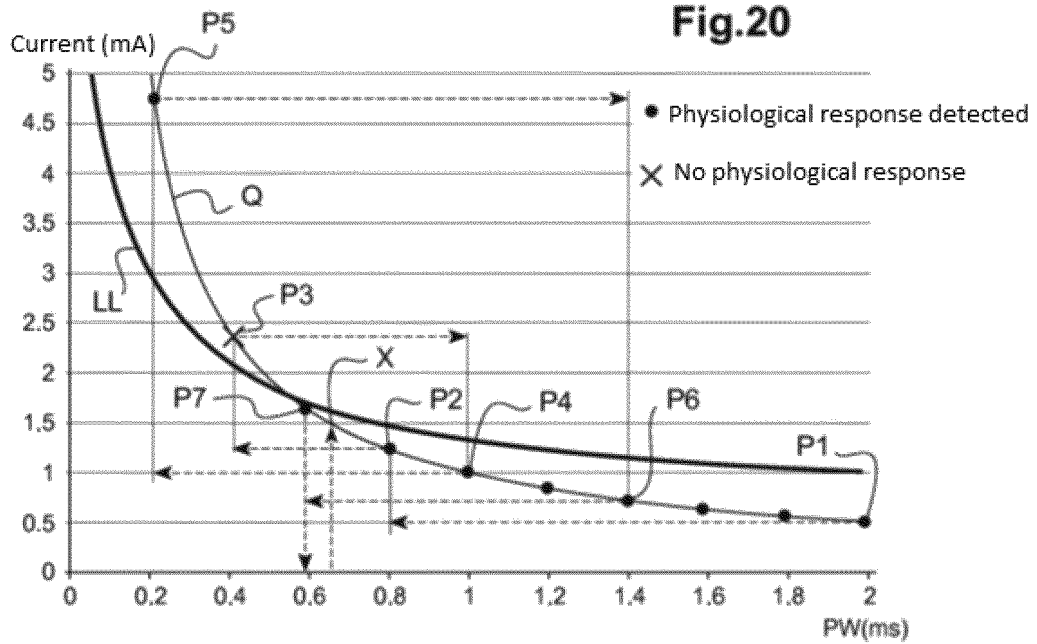
FIG. 20 is similar to FIG. 19, for an algorithm of the pseudo-stochastic type.

FIG. 19 shows a first technique for searching for the optimum point, this technique being based on an algorithm of the dichotomic iterations type, and FIG. 20 shows a second technique, based on an algorithm of the pseudo-stochastic type (i.e. stochastic while excluding the points already tested).

In both cases, the idea is to evaluate the position of the pivot point X with the fewest iterations possible.

These figures show a superposition of the isochrone characteristic curve Q with the Lapicque's Law curve LL, the dots corresponding to points situated below the Lapicque's curve LL, i.e. points for which no physiological response has been detected, and the crosses corresponding to points situated above the Lapicque's Law curve LL, i.e. points for which a physiological response has been detected.

The various iterations are designated, in order, by $P_1$, $P_2$, $P_3$ . . . In the dichotomic algorithm of FIG. 19, the abscissa of the point $P_{i+1}$ is determined as being 90% of the abscissa of the point $P_i$ in the absence of expected physiological response (i.e. if the point is below the Lapicque curve LL), the abscissa of $P_{i+1}$ being such that the abscissa of $P_i$ is 80% of the abscissa of $P_{i+1}$ otherwise. In the pseudo-stochastic algorithm of FIG. 20, the abscissas of the points are determined by a random draw, while excluding the points already tested.

Figure 21:
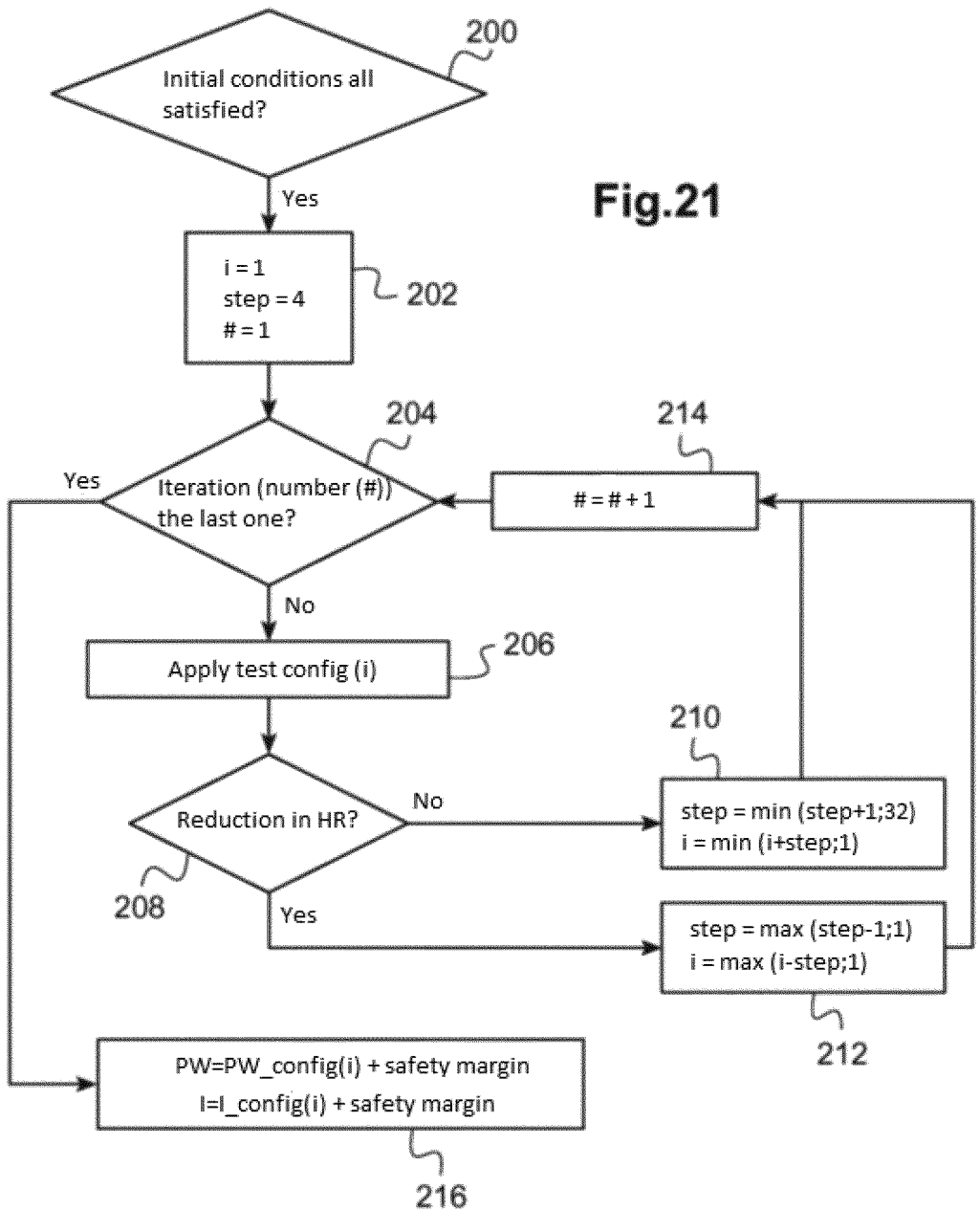
FIG. 21 is a flow chart showing the main steps in a search technique for seeking the optimum point by using an algorithm of the step-by-step type.

FIG. 21 shows the various steps in another search algorithm for searching for the pivot point, for a third technique implementing a search of the "step-by-step" type. The contents of steps 200 to 216 and how they follow on from one another are indicated directly in FIG. 21.

Figure 22:
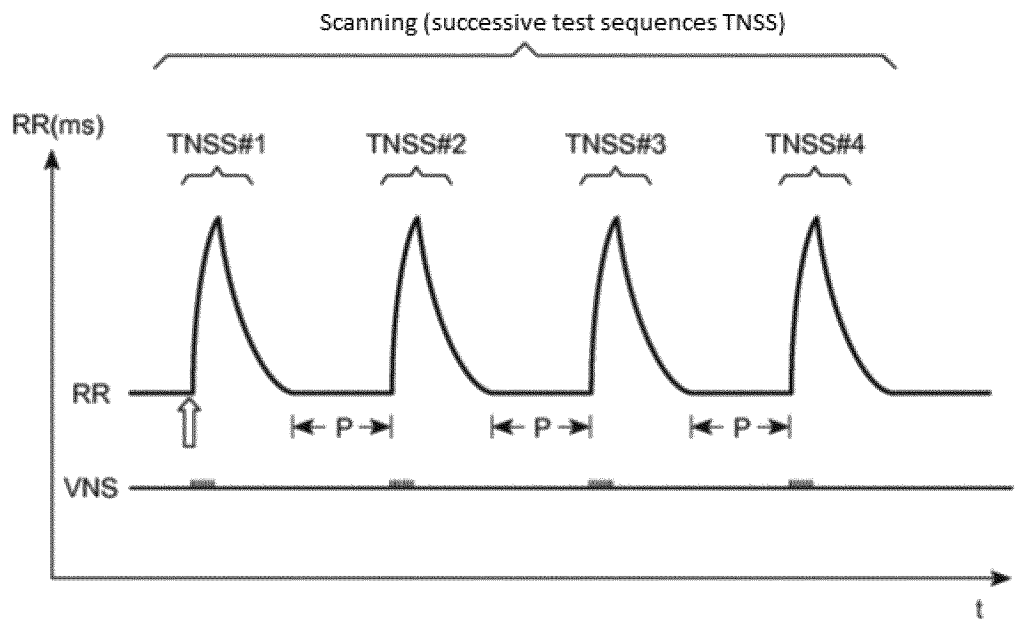
FIG. 22 shows the variations in heart rate induced by successive bursts of a test sequence.

FIG. 22 shows the variations in heart rate induced by successive bursts of a test sequence.

Regardless of the technique implemented, for each {pulse width, current} pair of values, the test sequence is applied one or more times, each sequence preferably being repeated a predetermined number of times while making provision, between each test sequence TNSS, for a "purge" period P making return possible for the tested physiological parameter (in this figure, the RR intervals measuring the heart rate in order to avoid any cumulative effect between successive test sequences).

Figure 23:
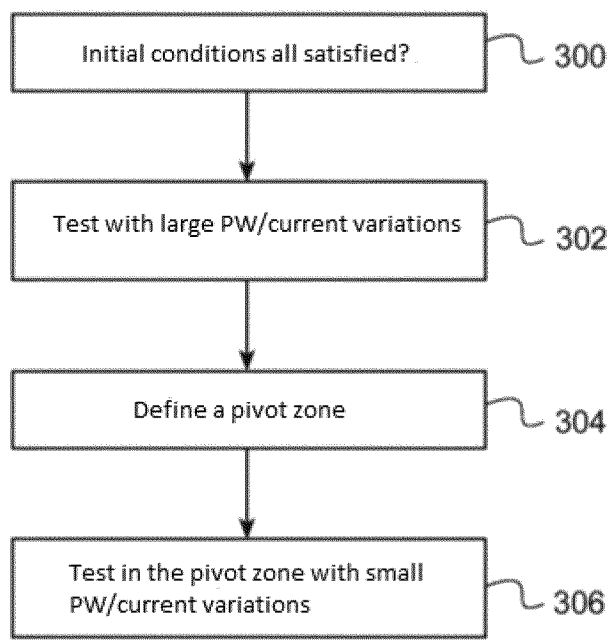
FIG. 23 is a flow chart showing the main steps in seeking the optimum point by testing large and then small variations on the current/pulse-width curve.
Figure 24:
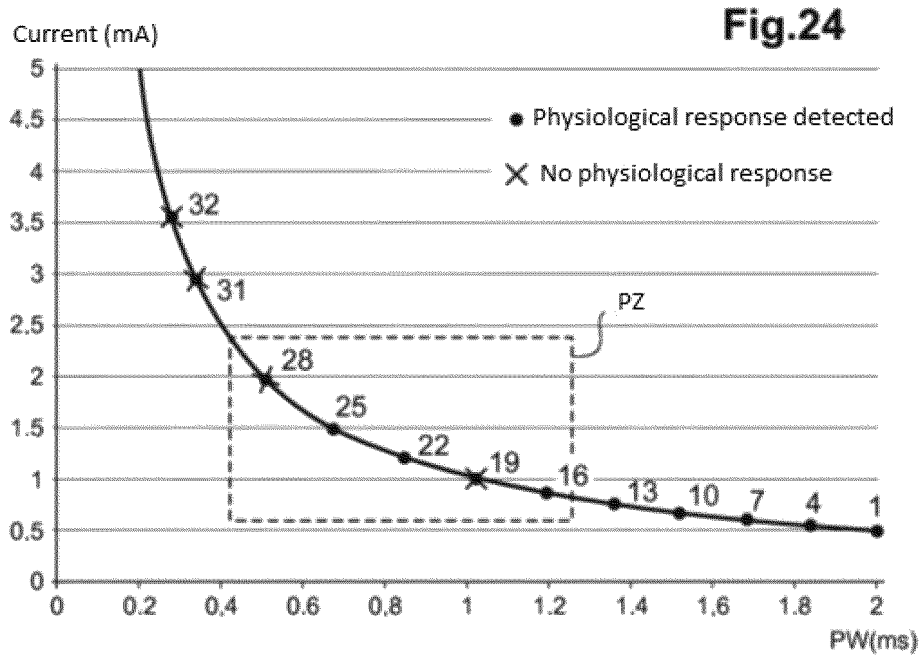
FIGS. 24 and 25, on a current/pulse-width graph, show the search technique of FIG. 23 on an iso-charge characteristic curve, respectively for large variations and for small variations on said curve.
Figure 25:
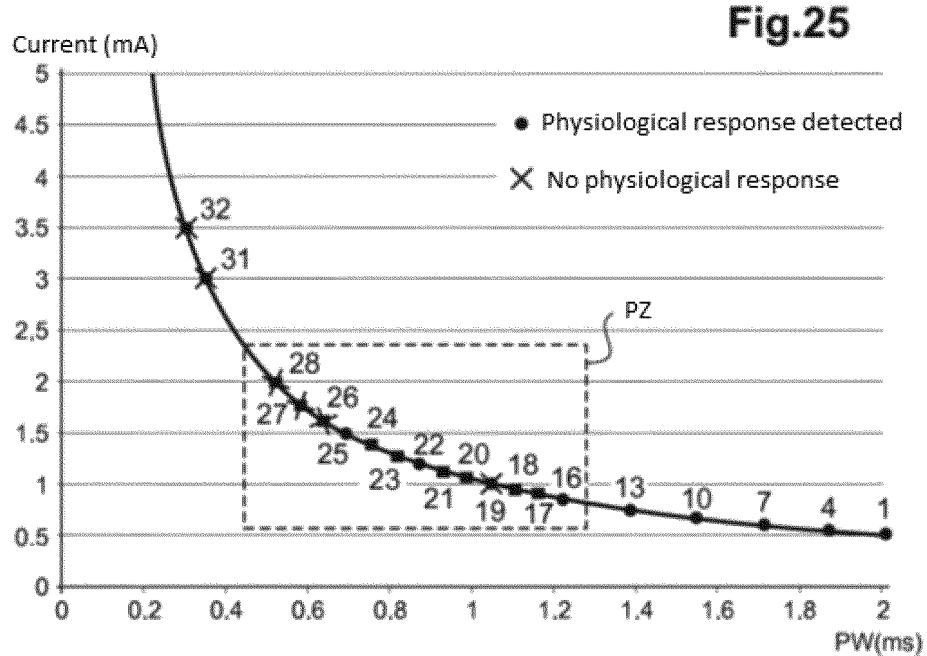

FIGS. 23 to 25 show a fourth technique consisting, in a first stage, in determining roughly on the {pulse width, current} curve a pivot zone around the searched-for pivot point, and, secondly, in second stage, in searching for the pivot point by fine variations restricted to the domain of the pivot zone.

FIG. 23 shows the main steps in such an algorithm.

The algorithm starts (block 300) by determining the optimum instant for performing the scanning, by checking that the initial conditions are all satisfied (as in step 100 of FIG. 15 or as in step 200 of FIG. 21).

The following step (block 302) consists in performing a first scanning test by going along the pulse width/current curve with large steps, e.g. steps of 3 index values of Table 1 above, i.e. going from 3 index values to the next 3 index values.

Such quick scanning is shown in FIG. 24, in which the points corresponding to the index values 1, 4, 7, 10, 13, etc. of Table 1 are indicated. This scanning may be performed by one of the above-described techniques (dichotomic, pseudo-stochastic, step-by-step), or any other method making it possible to converge towards the pivot zone PZ). In the example shown, the rough first scan is thus performed with only twelve different values of {pulse width, current} pairs.

On the basis of the results obtained (presence or absence of a physiological response detected for each measurement point), the pivot zone PZ is defined (block 304), e.g. on the basis of the highest configuration and of the lowest configuration (in index number, number being abbreviated herein to "No." or to "#") not producing any change in the physiological response. In the example shown, the lowest configuration is the one corresponding to index No. 16 (no change in response between the points 13 and 16) and the highest configuration is the one of index No. 28 (no change in the response between the point 28 and the point 31).

The process then continues (block 306) by implementing one of the above-described techniques (dichotomic, pseudo-stochastic, step-by-step or some other type of search), but restricted to the domain of the pivot zone PZ, as shown in FIG. 25.

This search is performed with a fine step, of one index unit, but only over a restricted range of Table 1. In the example shown in FIG. 25, it was determined in the preceding step that the pivot zone was bounded by the indices No. 16 and No. 28, so that the fine search is then effected only with {pulse width, current} pairs lying in the range index No. 17 to index No. 27.

Figure 26:
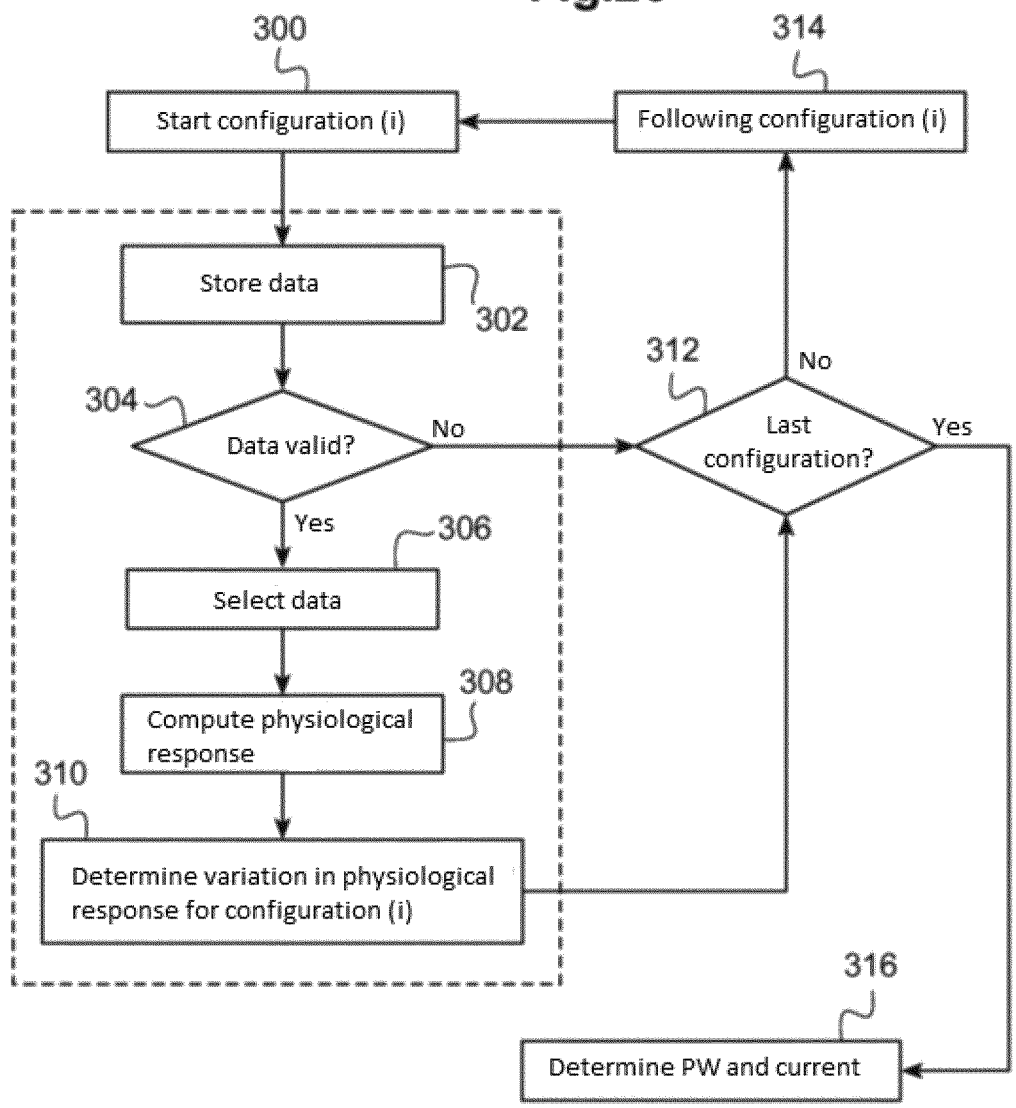
FIG. 26 is an overall flow chart presenting the successive steps in seeking the optimum configuration in accordance with the invention.

FIG. 26 is a general flow chart showing the successive search steps of the optimum configuration, as a function of the variations in the physiological response in the various configurations.

The flow chart starts at step 300, for a configuration i.

The data produced by the sensor(s) for sensing the physiological and/or physical value reflecting the physiological response are stored in a memory (block 302), optionally with those items of data that are most representative of the physiological response at that stages being selected from a plurality of items of data. The items of data are then validated (block 304) in such a manner as to exclude those that, for example, are obtained in the following cases:

at least one accelerated cardiac cycle, e.g. an increase in the parameter HR by more than 25% form one beat to the next;
at least one decelerated cardiac cycle, e.g. with the parameter HR having decreased by more than 25% of a following cycle;
patient in activity, e.g. when the acceleration sensor indicates an increased level, higher than a predetermined threshold; and
expiry of an authorized duration, e.g. a given time, within which to execute the algorithm.

If the items of data are validated, it is optionally possible to make a selection (block 306), e.g. by keeping only the last x cycles of the purge period and the last y cycles of the stimulation period. The physiological response is then calculated (block 308), e.g. by determining a mean or a median of the validated and selected items of data.

It is then possible to determine (block 310) the variations in the physiological response for the configuration i in question.

If the configuration is not the last one (block 312), the following configuration i+1 is selected (block 314) and the algorithm of blocks 300 to 310 is reiterated for this new configuration.

Once the last configuration has been reached, the pulse width and the current of the compensatory phase are determined (block 316), i.e. an index of Table 1 is chosen, optionally with a safety margin being applied, consisting in increasing the index by two units. For example, if the boundary pulse width and current values are obtained for index No. 5 (0.9 ms/1.11 mA) corresponding to the items of data that are closest to the pivot point X, then the values actually applied for the width and the current of the pre-charge pulse are the ones corresponding to index No. 7 (1.1 ms/0.91 mA).

In an implementation of the invention, the selected parameters are sent automatically via the home monitoring at regular intervals. In another implementation, the parameters are sent only if they exceed certain limit values considered to be abnormal.

In a multipolar configuration, a plurality of current generators are used. Each one potentially has its own stimulation profile, comprising stimulation and compensatory phases.

In a first embodiment, each compensatory phase of each generator is managed independently from the other phases and generators, on its duration (pulse width) and current parameters.

In a second embodiment, the compensatory phases are managed proportionally to the injection of charges of the respective stimulation phase. For example, if the compensatory phases need to be reduced by 1 µC, the compensatory phase of a pole delivering 80% of the current is reduced by 0.8 µC (reduction in current and/or duration).

The invention claimed is:

1. An active medical device, comprising:
   a generator configured to generate functional electrical neurostimulation and produce at least one multi-phase neurostimulation pulse train as output;
   a stimulation lead designed to be disposed on or in the vicinity of a structure of the nervous system of a patient wearing the device and for applying neurostimulation pulse trains to said structure;
   at least one sensor configured to deliver a monitoring signal representative of a physiological and/or physical parameter that can be influenced by the delivery of the at least one neurostimulation pulse train; and
   an automatic control circuit configured to automatically control charge compensation, wherein the circuit receives the monitoring signal delivered by the at least one sensor;
   wherein the at least one pulse train comprises:
      at least one stimulation pulse; and
      at least one compensatory pulse comprising:
         a pre-charge pulse preceding the stimulation pulse and/or a post-charge pulse following the stimulation pulse; and
         a passive discharge pulse terminating the pulse train,
      wherein the stimulation and compensatory pulses are current pulses in which the direction, the duration, and the amplitude are controlled, and wherein the at least one compensatory pulse procures a cumulative electric charge that compensates for the electric charge of the at least one stimulation pulse;
   wherein the automatic control circuit is configured to:
      determine an amplitude and/or a duration for the at least one compensatory pulse as a function of at least one predetermined criterion; and
      deliver, to the generator, a control signal for controlling the at least one compensatory pulse to be produced as output by said generator.

2. The device of claim 1, wherein the automatic control circuit is further configured to:
   control the generator in such a manner as to produce at least one test pulse train;
   collect the monitoring signal after the end of the at least one test pulse train;
   determine, based on the level of the monitoring signal, whether or not a physiological and/or physical effect is produced by applying the test pulse train; and
   determine the amplitude and/or the duration of the compensatory pulses of the following pulse trains as a function of the result of the determination.

3. The device of claim 2, wherein the test pulse train comprises a pre-charge pulse followed by at least one stimulation pulse.

4. The device of claim 3, wherein the automatic control circuit is further configured to deliver a single test pulse train and collect the monitoring signal immediately after the end of the test pulse train.

5. The device of claim 4, wherein the automatic control circuit is further configured to deliver a plurality of successive test pulse trains and collect the monitoring signal after the end of the last test pulse train of said plurality of successive test pulse trains.

6. The device of claim 2, wherein the test pulse train comprises a pre-charge pulse but does not comprise stimulation pulse.

7. The device of claim 2, wherein the automatic control circuit is further configured to determine the amplitudes and/or the durations of the compensatory pulses of the current pulse trains as a function of the maximum amplitude of the passive discharge pulse (PD) measured for the test pulse train.

8. The device of claim 1, wherein the automatic control circuit is further configured to control a time interval between the end of the stimulation pulse and closure of switches for putting the stimulation electrodes at the same potential, in such a manner as to modulate the starting instant of the passive discharge pulse.

9. The device of claim 1, wherein the automatic control circuit is further configured to control a time interval between the end of the pre-charge pulse and the start of the stimulation pulse.

10. The device of claim 1, wherein the automatic control circuit is further configured to control a time interval between the closure and the opening of switches for putting the stimulation electrodes at the same potential, in such a manner as to modulate the duration of the passive discharge pulse.

11. The device of claim 1, wherein the sensor is a sensor configured to measure a parameter, wherein the parameter is at least one of an electrical activity of the heart, an electrical activity of the nervous system, a heart rate, a respiratory rate, an electric current flowing through a tissue, an acceleration of the patient's body, a blood pressure, an endocardial acceleration, or a position of the patient.

* * * * *